United States Patent [19]

Thornfeldt

[11] Patent Number: 4,816,478
[45] Date of Patent: Mar. 28, 1989

[54] TREATMENT OF ACQUIRED IMMUNODEFICIENCY SYNDROME

[76] Inventor: Carl R. Thornfeldt, 1054 N.W. 2nd Ave., Ontario, Oreg. 97914

[21] Appl. No.: 88,437

[22] Filed: Aug. 24, 1987

[51] Int. Cl.$^4$ .......................................... A61K 31/335
[52] U.S. Cl. .................................................. 514/450
[58] Field of Search ....................................... 514/450

[56] References Cited

PUBLICATIONS

Chemical Abstracts, 99: 187025w, (1983).
Chemical Abstracts, 99: 187026x, (1983).
Chemical Abstracts, 101: 103526j, (1984).
Chemical Abstracts, 103: 189143h, (1985).

Primary Examiner—Jerome D. Goldberg
Attorney, Agent, or Firm—Townsend and Townsend

[57] ABSTRACT

A treatment of Acquired Immunodeficiency Syndrome (AIDS) and AIDS Related Complex (ARC) with therapeutically effective amounts of semisynthetic derivatives of dihydroartemesinin and synthetic compounds with a sesquiterpene structure.

2 Claims, No Drawings

TREATMENT OF ACQUIRED IMMUNODEFICIENCY SYNDROME

BACKGROUND

This invention relates to the treatment of Aquired Immunodeficiency Syndrome (AIDS) and AIDS Related Complex (ARC) with synthetic or semisynthetic compounds containing sesquiterpenes. Specifically, treating with dihydroartemisinin propylcarbonate, sodium artesunate, artemether and a synthetic compound containing a sesquiterpene, namely artelinic acid.

AIDS and ARC form the disease spectrum of a Human Immunodeficiency Virus (HIV) infection, a recently mutated virus producing a pandemic. This virus suppresses Cell Mediated Immunity (CMI) and destroys T lymphocytes, the major defense against invading virus, fungal, and parasitic organisms and malignant cells. These subjects die because of overwhelming infection and metastatic cancer. Any effective drug for AIDS must stimulate CMI, stop cells, have marked long term safety, be inexpensive, and minimize human toxicity. Treatment difficulty centers on the constantly changing viral capsid and the long incubation period (5-15 years). Only one drug Azidothymidine (AZT) has been proven effective against AIDS, but not ARC. The outlook for a vaccine is also dismal.

This invention uses a synthetic sesquiterpene, artelinic acid, or semisynthetic derivatives of dihydroartemesinin (carbonates, sulfonates, ethers, esters) as active compounds to treat AIDS and ARC. Artemisinin has been used as a tea for 3 centuries for malaria and hemorroids and is extremely safe for humans. The semisynthetic derivatives have much more potent antimalarial activity but less safety. Different Chinese researchers have found artemesinin stimulates CMI, suppresses malignancy, and has in vivo virustatic activity against influenza, each to varying degrees.

SUMMARY

It has now been discovered conceptually that AIDS/ARC can be successfully suppressed safely with chronic administration of systemic doses of semisynthetic derivatives of dihydroartemisinin, including ethers, esters, carbonates, and sulfonates, and with synthetic analogs, such as artenilic acid.

DETAILED DESCRIPTION OF THE INVENTION

The semisynthetic derivatives of dihydroartemisinin contain a sesquiterpene lactone with an attached peroxide of the following structure:

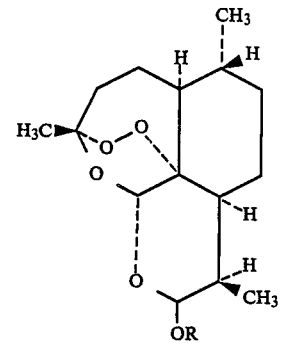

Carbonate: $R = C(=O)$ O-alkyl or -aryl
Ester: $R = C (=O)$ -alkyl or -aryl
Ether: $R = $ alkyl
Sulfonates: $R = S(=O)$ O-alkyl or -aryl These derivatives were developed to improve the antimalarial efficacy, decrease disease recrudesence, and improve stability.

The carbonates, sulfonates, and ethers are all soluble in peanut oil, while the esters require sodium bicarbonate and saline for solubility. All of these compounds and artelinic acid are administered systemically. The peanut oil products are given intramuscularly at a dose of 0.8 grams and the ester (artesunate) was given 1.2 grams intravenously, or 3.2 grams orally.

The dose used at this time is not critical, as it depends on the formulation and method of administration. Generally 0.25 grams to 6.4 grams per dose will be used to treat AIDS and ARC.

The term "therapeutically effective amount" will denote the amount used to produce a substantial improvement in the treated diseases when used for a long period of time. The appropriate amounts will be determined by experimentation. Numerous variations in the formulations may be made without departing from the spirit and scope of the invention.

What is claimed is:

1. A method of the treatment of a human subject suffering from AIDS or ARC comprising systemically administering to said subject a composition containing an artelinic acid in an amount therapeutically effective in said treatment.

2. A method for the treatment of a human subject suffering from AIDS or ARC comprising systemically administering to said subject a composition containing a member selected from the group consisting of artemether, artesunate, propyl carbonate dihydroartemisinin, and dihydroartemisinin, in an amount therapeutically effective in said treatment.

* * * * *